United States Patent
Han et al.

(10) Patent No.: US 8,206,760 B2
(45) Date of Patent: Jun. 26, 2012

(54) **COMPOSITION FOR INHIBITION OF TRANSPLANT REJECTION CONTAINING THE *CORDYCEPS MYCELLIA* EXTRACT AS AN ACTIVE INGREDIENT**

(75) Inventors: Man Woo Han, Daejeon (KR); Jae Kuk Yoo, Daejeon (KR); Chang-Uk Hur, Daejeon (KR); Hwan-Chul Kim, Daejeon (KR); Jin Pyo Kim, Daejeon (KR)

(73) Assignee: Hankook Pharm. Co., Inc., Nonsan-Si, Chungcheongnam-Do (KR)

( * ) Notice: Subject to any disclaimer, the term of this patent is extended or adjusted under 35 U.S.C. 154(b) by 0 days.

(21) Appl. No.: 13/161,958

(22) Filed: Jun. 16, 2011

(65) Prior Publication Data

US 2011/0243970 A1  Oct. 6, 2011

Related U.S. Application Data

(63) Continuation of application No. 12/740,139, filed as application No. PCT/KR2007/006356 on Dec. 7, 2007, now abandoned.

(51) Int. Cl.
*A01N 65/00* (2009.01)

(52) U.S. Cl. .................................................. 424/725

(58) Field of Classification Search .................. None
See application file for complete search history.

(56) References Cited

U.S. PATENT DOCUMENTS

| 4,117,118 A | 9/1978 | Harri et al. |
| 2010/0285053 A1 * | 11/2010 | Lee et al. ............. 424/195.15 |

FOREIGN PATENT DOCUMENTS

| KR | 1020050051179 A | 6/2005 |
| KR | 1020060092373 A | 8/2006 |

OTHER PUBLICATIONS

International Search Report and Written Opinion PCT/KR2007/006356 dated Aug. 19, 2008.

* cited by examiner

*Primary Examiner* — Michael Meller
(74) *Attorney, Agent, or Firm* — Lucas & Mercanti, LLP

(57) ABSTRACT

Disclosed is a composition for the inhibition of transplant rejection and the treatment of skin diseases, comprising a *cordyceps mycellia* extract as an active ingredient. The *cordyceps mycellia* extract significantly suppresses the production of antibodies to transplants without side effects, such as weight change. Based on natural material, the composition is non-toxic and harmless to the human body and thus can be used as an immunosuppressant for organ transplantation. Also, it stops oozing from sores and is useful in the treatment of skin diseases, including atopy, allergic reactions, decubitus ulcers, pemphigus and smallpox.

4 Claims, 5 Drawing Sheets

COMPOSITION FOR INHIBITION OF TRANSPLANT REJECTION CONTAINING THE *CORDYCEPS MYCELLIA* EXTRACT AS AN ACTIVE INGREDIENT

CROSS REFERENCE TO RELATED APPLICATIONS

This patent application is a continuation application of U.S. patent application Ser. No. 12/740,139 filed on Apr. 28, 2010, which is a 371 of PCT/KR2007/006356 filed Dec. 7, 2007, the contents of each of which are incorporated herein by reference.

TECHNICAL FIELD

The present invention relates to a composition for inhibition of transplant rejection, comprising a cordyceps mycellia extract as an active ingredient.

BACKGROUND ART

Transplant rejection occurs when the immune system of the recipient of a transplant attacks a transplanted organ or tissue. Thus, effective suppression of the immune response is known as a main factor determining the success of transplantation. In this regard, the development of immunosuppressive medications has brought about exceptional advances in the transplantation of organs and tissues and the treatment of autoimmune diseases and has made a great contribution to the study of the in vivo mechanism of immune responses to the transplanted organ or tissue.

As described, immunosuppressive drugs were developed to inhibit or attenuate transplant rejection. An example is cyclosporine A (U.S. Pat. No. 4,117,118) produced from *Tolypocladium inflatum*, a soil fungus. These immunosuppressive drugs not only help realize clinically successful organ transplantation, but also suggest the therapeutic use thereof in treating autoimmune diseases. Even though they are required to act selectively and specifically for T-cells only, conventional immunosuppressive drugs have an influence on a wide range of cellular functions, including general signal pathways, causing side effects on other organs, which are healthy (see. S.-H. Lee et al., Korean J. Immunology, 19:375~389 (1997)). For instance, cyclosporine A is known to show side effects of chronic liver diseases and hypertension after heart transplantation (see: J. E. F. Reynolds, et al., Martindale The Extra Pharmacopoeia, 31$^{st}$ ed., pp. 557-562, Royal Pharmaceutical Society, London, 1996). Many attempts have been made to develop novel immunosuppressive drugs free of side effects. FK-506 has recently been discovered to be an immunosuppressant, and has been commercialized. However, side effects of this drug have also been found (Clin. Transplantation, 11: 237~242 (1997)).

In China, vegetable worms, together with Korean ginseng, have long been used as precious materials in medicinal cuisine for special people in the aristocratic classes. Vegetable worms are a kind of medicinal fungus produced as a result of the parasitism of vegetable worms on insects. In high temperature and moisture conditions, the vegetable worms, which are actually fungus, infect living insects, proliferate therein to kill the host insects, and form fruiting bodies on the surface of the host insects. As used herein, the term "vegetable worm", is intended to primarily refer to *Cordyceps sinensis*, a parasite on larvae of the Hepialidae family, but at present generally refers to all fungi attacking arthropods, such as spiders.

*Cordyceps sinensis* breaks down into 10.8% water, 8.4% lipids, 25~32% crude proteins, 23.9% carbohydrates, and 18.5% crude fibers. In this vegetable worm are found 17 different amino acids, including 8 essential amino acids. Also, it contains a trace amount of cordycepin, 7.6% of D-mannitol and 11.2% of polysaccharides, all known as medicinally active materials. Cordycepin, a derivative of the nucleoside adenosine, is an isomer of quinic acid, known to show anti-cancer activity.

Various medicinally valuable activities of extracts from vegetable worms discovered thus far include antibacterial activity (*Staphylococcus, Streptococcus, Bacterium mallei, Bacillus anthracis, Pasteurella suiseptica, Microsporum gypseum*, and *Microsporum lanosum*), activity on the central nervous system (sedative, anticonvulsant activity), the respiratory system (bronchial asthma healing, expectorant activity) and the cardiovascular system (stabilization of heart beats, reduction of cholesterol level, anti-hypoxia activity), anticancer activity, immuno potentiation, anti-fatigue activity, and anti-aging activity.

However, nowhere has the use of vegetable worm extracts as an immunosuppressant been disclosed in the prior art.

Leading to the present invention, intensive and thorough research on an immunosuppressant entailing no side effects, conducted by the present inventors, resulted in the finding that an extract from vegetable worm mycelia significantly inhibits the immune response to transplanted organs or tissues.

DISCLOSURE

Technical Problem

It is therefore an object of the present invention to provide an immunosuppressive composition, useful in the prevention of transplant rejection, comprising a cordyceps mycellia extract as an active ingredient.

It is another object of the present invention to provide a composition for the prevention and treatment of skin diseases, comprising a cordyceps mycellia extract as an active ingredient.

Technical Solution

In order to accomplish the objects of the present invention, an immunosuppressive composition comprising a mycelial extract from a vegetable worm as an active ingredient is provided for the inhibition of transplant injection.

Also, a composition comprising a cordyceps mycellia extract as an active ingredient is provided for the prevention and treatment of skin diseases.

Advantageous Effects

The cordyceps mycellia extract was found to significantly suppress the production of antibodies to transplants without side effects, such as weight change. Based on a natural material, the composition is non-toxic and harmless to the human body, and thus can be used as an immunosuppressant for organ transplantation. Also, it arrests oozing from sores and is applicable to the prevention and treatment of skin diseases, including atopy, allergic reactions, decubitus ulcers, pemphigus and smallpox.

BEST MODE

Figure 1:
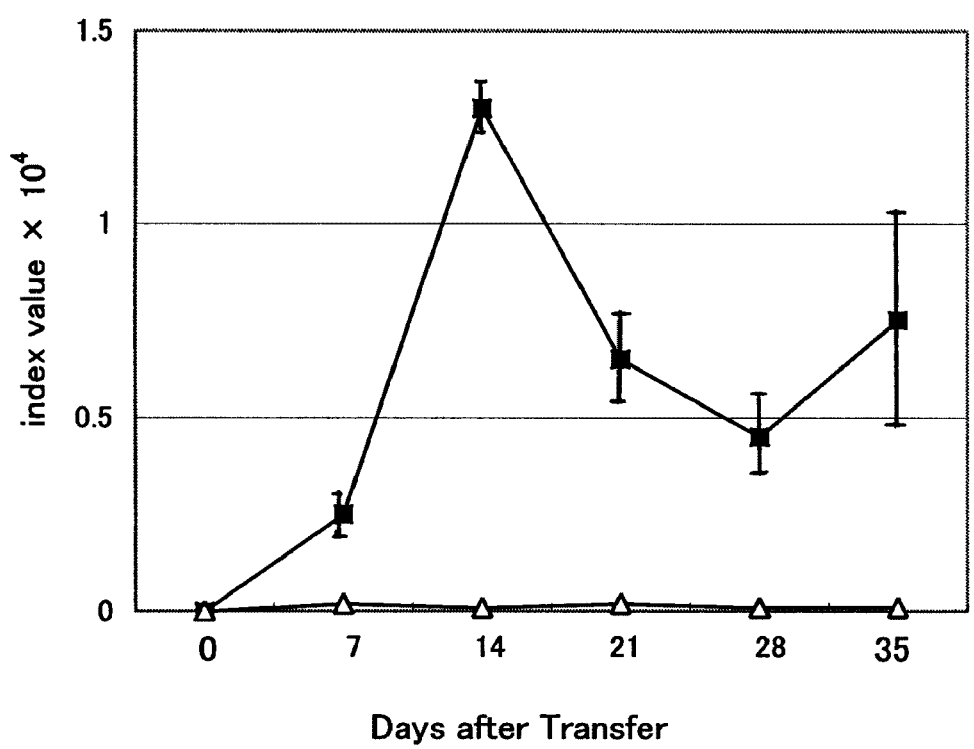
FIG. 1 is a graph showing the levels of antibodies produced against splenocytes transplanted into mice administered with the cordyceps mycellia extract of the present invention or with saline in accordance with an embodiment of the present invention (■: control, Δ: experimental group).

In accordance with an aspect of the present invention, an immunosuppressive composition based on a cordyceps mycellia extract is provided for the inhibition of transplant rejection.

The cordyceps mycellia extract may be obtained from cultured mycelia, or may be commercially available. For example, vegetable worm powder, which is sold as a health aid food, may be used in the present invention, whether it comes from fruit bodies, mycelia, or a combination thereof.

Examples of the vegetable worm useful in the present invention include *Cordyceps militaris, Cordyceps sinensis*, which is parasitic on larvae of the Hepialidae family, *Hymenostilbe odonatae, Cordyceps nutans, Tilachlidiopsis nigra, Paecilomyces japonica, Cordyceps tricentri*, and *Cordyceps sphecocephala.*

The cordyceps mycellia extract according to the present invention was tested for immunosuppressive effect on smallpox mouse models. After the transplantation of splenocytes thereinto, the animal models were administered with the cordyceps mycellia extract. ELISA analysis on the animal models for the quantification of antibodies to the splenocytes indicated that the cordyceps mycellia extract of the present invention significantly inhibits the production of the antibodies (see FIGS. 1 and 4). Therefore, the cordyceps mycellia extract according to the present invention can be used as an immunosuppressant for the prevention of transplant rejection.

Also, observations were made of whether the cordyceps mycellia extract causes side effects in vivo. Almost no changes were found in the weight of the mice after the transplantation of splenocytes (see FIGS. 2 and 5). Hence, the cordyceps mycellia extract can be used as an immunosuppressant for the prevention of transplant rejection without the occurrence of side effects, such as changes in weight, upon organ transplantation.

In accordance with another aspect thereof, the present invention provides a composition for the prevention and treatment of skin diseases, comprising a cordyceps mycellia extract as an active ingredient.

The cordyceps mycellia extract according to the present invention was tested for therapeutic activity for skin diseases on smallpox mouse models. After the administration of the cordyceps mycellia extract thereinto, the smallpox mouse models were observed to stop oozing from the smallpox sores (FIG. 3). In contrast, the control, which was not administered with the cordyceps mycellia extract of the present invention, was observed to ooze from the smallpox sores and remain depilated at the sores. Hence, the cordyceps mycellia extract according to the present invention can be used for the treatment of skin diseases, such as atopy, allergic reactions, decubitus ulcers, pemphigus, smallpox, etc.

When used as medications or health aid foods, the composition may further comprise one or more active ingredients having a function similar to that of the cordyceps mycellia extract.

The cordyceps mycellia extract in accordance with the present invention can be administered orally or non-orally, and may be provided in general medicinal forms. For clinical practice, the cordyceps mycellia extract of the present invention may be used in oral or non-oral forms. It is usually formulated in combination with a diluent or an excipient, such as a filler, a thickening agent, a binder, a wetting agent, a disintegrant, a surfactant, etc. Solid agents intended for oral administration of the extract of the present invention may be in the form of tablets, pills, powders, granules, capsules, and the like. In these solid agents, the cordyceps mycellia extract of the present invention is formulated in combination with at least one excipient, such as dextrin, starch, calcium carbonate, sucrose, lactose, or gelatine. In addition, a lubricant, such as magnesium stearate, talc, or the like, may also be added. Liquid agents intended for oral administration include suspensions, internal use solutions, emulsion, syrups, and the like. In addition to a simple diluent, such as water or liquid paraffin, various excipients, such as wetting agents, sweetening agents, aromatics, preservatives, and the like, may be contained in the liquid agents for the oral administration of the extract of the present invention. Also, non-oral dosage forms of the extract of the present invention include sterile aqueous solutions, non-aqueous solutions, suspensions and emulsions, freeze-dried agents, and suppositories. Non-aqueous solutions and suspensions made from propylene glycol, polyethylene glycol, vegetable oils, such as olive oil, and injectable esters such as ethyl oleate may be used. The basic materials of suppositories include Witepsol, macrogol, Tween 61, cacao butter, laurin, glycerol, and gelatin.

The effective dosage of the cordyceps mycellia extract in accordance with the present invention depends on various factors, including the patient's weight, age, gender, state of health, diet, the time of administration, route of administration, excretion rate, etc. For oral administration, the cordyceps mycellia extract in accordance with the present invention may be administered at a dose ranging from 550 to 2,200 mg/day.

For application to the treatment of skin diseases, the cordyceps mycellia extract of the present invention may be used alone or in combination with other therapies, including surgery, radiotherapy, hormonal therapy, chemical therapy and/or biological reaction regulators.

MODE FOR INVENTION

A better understanding of the present invention may be obtained in light of the following examples, which are set forth to illustrate, but are not to be construed to limit the present invention.

EXAMPLE 1

Immunosuppression Assay on Smallpox Mouse Model

An immunosuppression test was conducted with the cordyceps mycellia extract of the present invention on smallpox mouse models (obtained from Microbiology•Immunology Lab of the Medical College in Keio Univ.).

From two days before the transplantation of splenocytes (Dsg3−/−), five smallpox mice were administered orally with a cordyceps mycellia extract powder (Cordyma®; Han Kook Sin Yak) at a dose of 10 mg/kg/day. For 35 days (5 weeks) after the splenocyte transplantation, the cordyceps mycellia extract was orally administered at a dose of 10 mg/kg/day. For a control, physiological saline was used instead of the extract.

Blood samples were taken from the mice 7 days (1 week), 14 days (2 weeks), 21 days (3 weeks), 28 days (4 weeks) and 35 days (5 weeks) after the transplantation, and were analyzed using ELISA to determine the level of antibodies to the splenocytes. Throughout the experiment, the weights and skin states of the mice were monitored every day.

Figure 2:
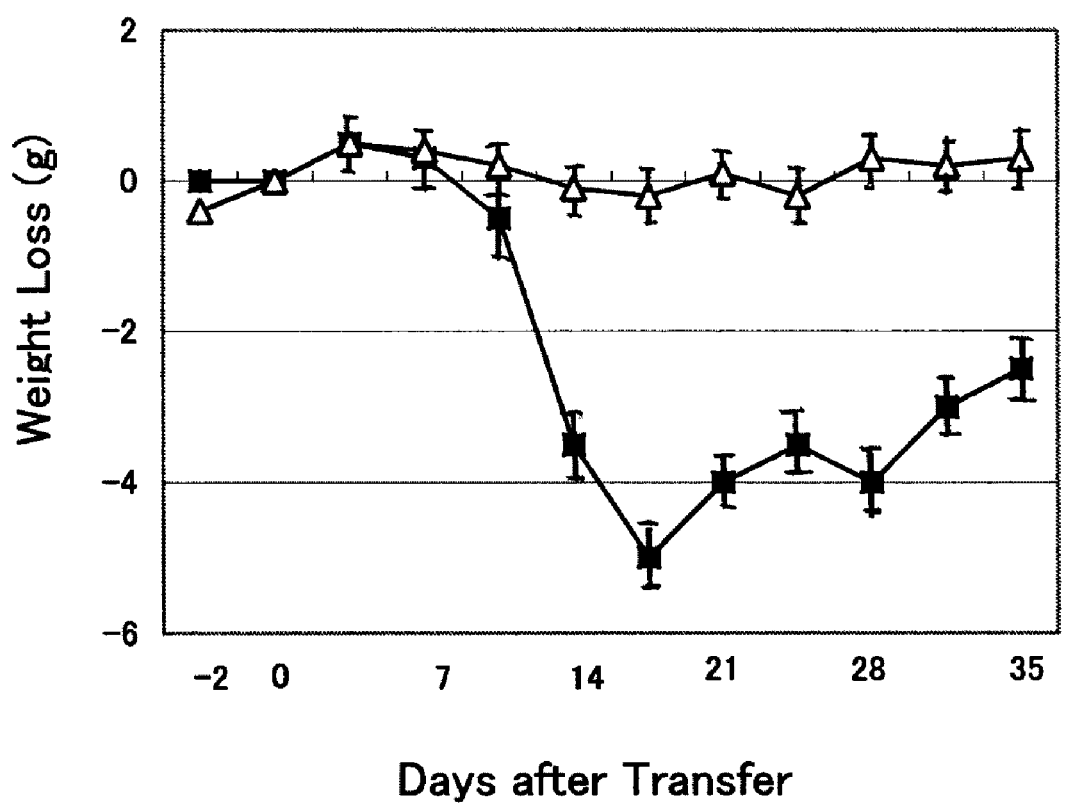
FIG. 2 is a graph showing changes in the weight of the mice administered with the cordyceps mycellia extract of the present invention and with saline in accordance with an embodiment of the present invention (■: control, Δ: experimental group).
Figure 3:
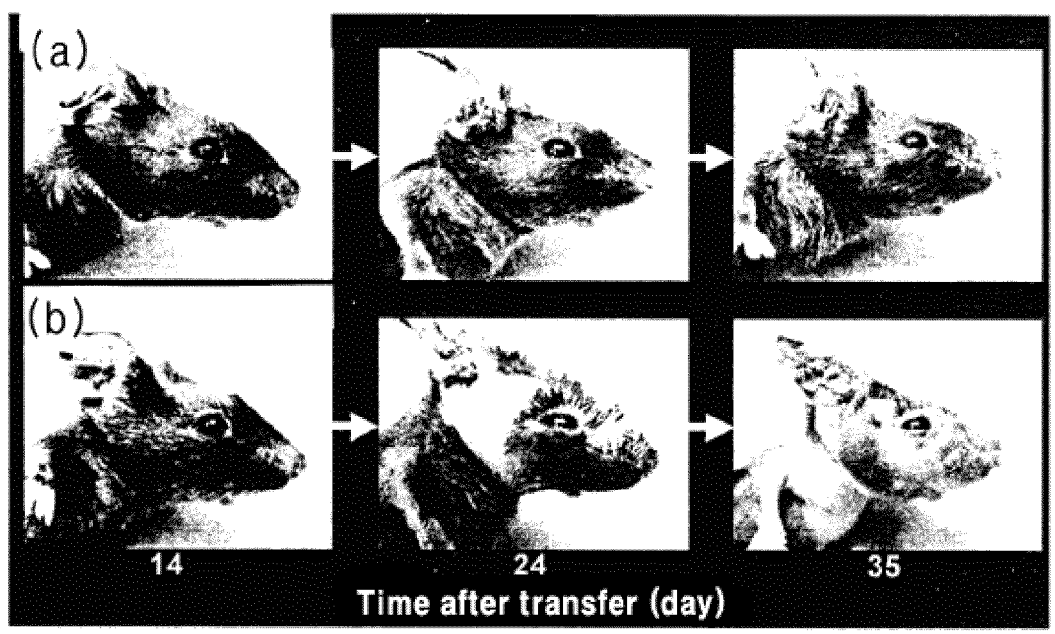
FIG. 3 shows the dermal states of mice administered with the cordyceps mycellia extract of the present invention and with saline in photographs (panel a: experimental group, panel b: control).

The results are depicted in FIGS. 1 to 3.

In FIG. 1, the levels of antibodies to the splenocytes are plotted against time for the experimental group and the control group. FIG. 2 shows changes in weight for the experimental group and the control group. In FIG. 3, the experimental group and the control group are compared with each other with respect to skin state.

As seen in FIG. 1, the level of antibodies to the transplanted splenocytes in the mice administered with the cordyceps mycellia extract of the present invention was almost zero. From this, it is apparent that the cordyceps mycellia extract according to the present invention effectively inhibits the production of antibodies to transplants.

In FIG. 2, it can be observed that the weight of the control administered with physiological saline slightly increased immediately after the transplantation, but sharply decreased from 7 days after the transplantation, as transplant rejection occurred. In contrast, almost no change was found in the weight of the mice administered with the cordyceps mycellia extract of the present invention. Demonstrated to effectively inhibit the transplant rejection and cause no side effects, such as weight gain, the composition comprising the cordyceps mycellia extract according to the present invention can therefore be used as an immunosuppressive medication applicable for organ or tissue transplantation.

Furthermore, as shown in FIG. 3, while the control suffered from sores due to smallpox, skin disease was suppressed in the mice administered with the cordyceps mycellia extract of the present invention. Hence, the cordyceps mycellia extract according to the present invention can be applied to the treatment of skin diseases including atopy, allergic reactions, decubitus ulcers, pemphigus, smallpox, etc.

EXAMPLE 2

Immunosuppression Assay on Pemphigus Mouse Model

An immunosuppression test was conducted with the cordyceps mycellia extract of the present invention on pemphigus mouse models, as follows.

Two S129 Dsg3−/− mice and 24 S129 Rag2−/− mice were prepared as transplantation donors and recipients, respectively. The recipient mice were divided into four groups of six: control (CMC administered), comparative group (cyclophosphamide (CPA) administered), experimental group 1 and experimental group 2 (cordyceps mycellia extract (Cordyma®; Han Kook Sin Yak) administered). The transplantation donor was subjected to an immune reaction by administering a Dsg3-His protein thereto, as described below.

First, 10 μg of mouse Dsg3-His protein was emulsified with the same amount of complete Freund's adjuvant (CFA) and subcutaneously injected into the mice ($1^{st}$). One week after the first immunization, an emulsion of 10 μg of mouse Dsg3-His protein in the same amount of incomplete Freund's adjuvant was subcutaneously injected ($2^{nd}$). One week after the $2^{nd}$ immunization, subcutaneous injection was carried out in the same manner as in the second immunization ($3^{rd}$). One week later, 10 μg of the protein was intraperitoneally administered ($4^{th}$) One week after the $4^{th}$ immunization, intraperitoneal injection was performed in the same manner as in the $4^{th}$ immunization ($5^{th}$). Three days before transplantation, intraperitoneal injection was performed in the same manner as in the $4^{th}$ immunization.

From one day before the transplantation of splenocytes (Dsg3−/−), oral administration was conducted with 1 ml of the cordyceps mycellia extract (Cordyma®; Han Kook Sin Yak) for each experimental group, 1 ml of CMC for the control group and 1 ml of cyclophosphamide for the comparative group. Thereafter, splenocytes were transplanted at a density of $1.5 \times 10^6$ cells/500 μl into each mouse, followed by oral administration of 1 ml of the test material to the mice on day zero, 1, 4, 7, 11, 14, 18, 21, 25, and 28 after the transplantation. Afterwards, blood samples were taken from the mice on day zero, 1, 4, 7, 11, 14, 18, 21, 25 and 28 after the transplantation, and were analyzed to determine the level of antibodies to the splenocytes using ELISA. Throughout the experiment, the weights and skin states of the mice were monitored every day.

The cordyceps mycellia extract (Cordyma®; Han Kook Sin Yak) for the experimental group 1 was prepared by placing 500 mg of a powder of *Isaria japonica* in a 15 ml tube, adding a 0.5% CM-Na solution (hereinafter referred to as "CMC") to the tube to form a total volume of 5 ml, and sonicating it for 30 min in a bath to form a suspension (dosage: 2000 mg/kg/administration). As for the experimental group 2, its cordyceps mycellia extract (Cordyma®; Han Kook Sin Yak) was prepared by mixing 0.5 ml of the cordyceps mycellia extract (Cordyma®; Han Kook Sin Yak) for the experimental group 1 with 4.5 ml of CMC and treating the mixture for 30 min in a sonication bath to give a suspension (dosage: 200 mg/kg/administration).

Also, the cyclophosphamide administered to the comparative group was a suspension prepared by pulverizing 50 mg of the Endoxan P tablet, commercially available from Shionogi Pharmaceutical Corporation, mixing the powder with 16.7 ml of CMC, and sonicating the mixture in a bath for 30 min (dosage: 60 mg/kg/administration).

Their dermal conditions were examined on the abdominal side, the dorsal side, the right side, and the left side for blistering, depilation and swelling with the naked eyes while pictures were taken of the entire dorsal side and three facial sides (right, left and chin) with a digital camera for more precise monitoring.

Figure 4:
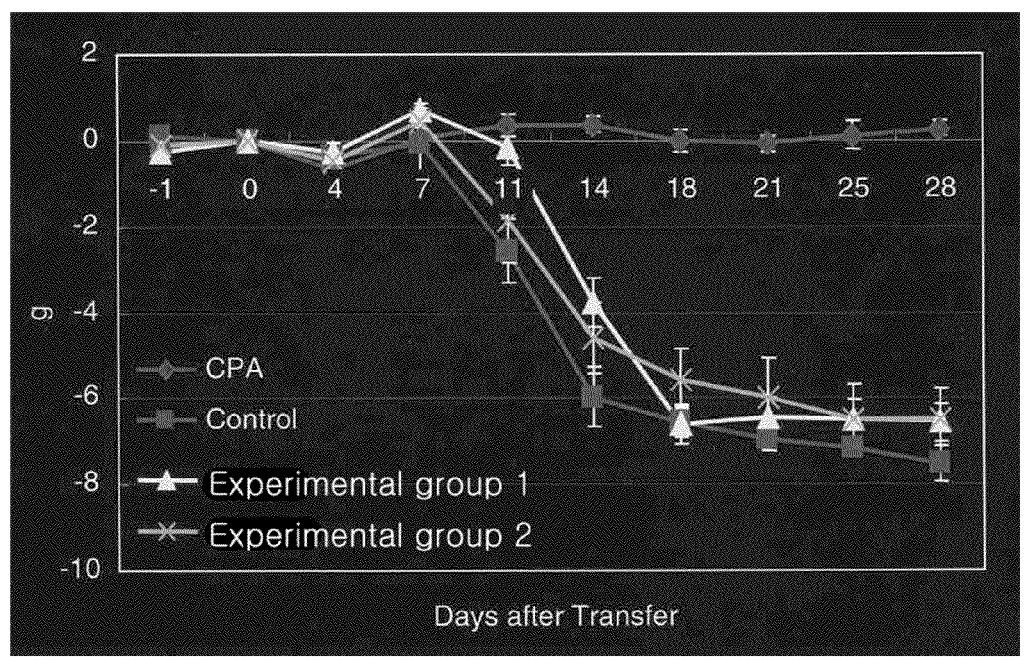
FIG. 4 is a graph showing the levels of antibodies produced against splenocytes transplanted into mice administered with the cordyceps mycellia extract of the present invention or with other comparative chemicals in accordance with another embodiment of the present invention.
Figure 5:
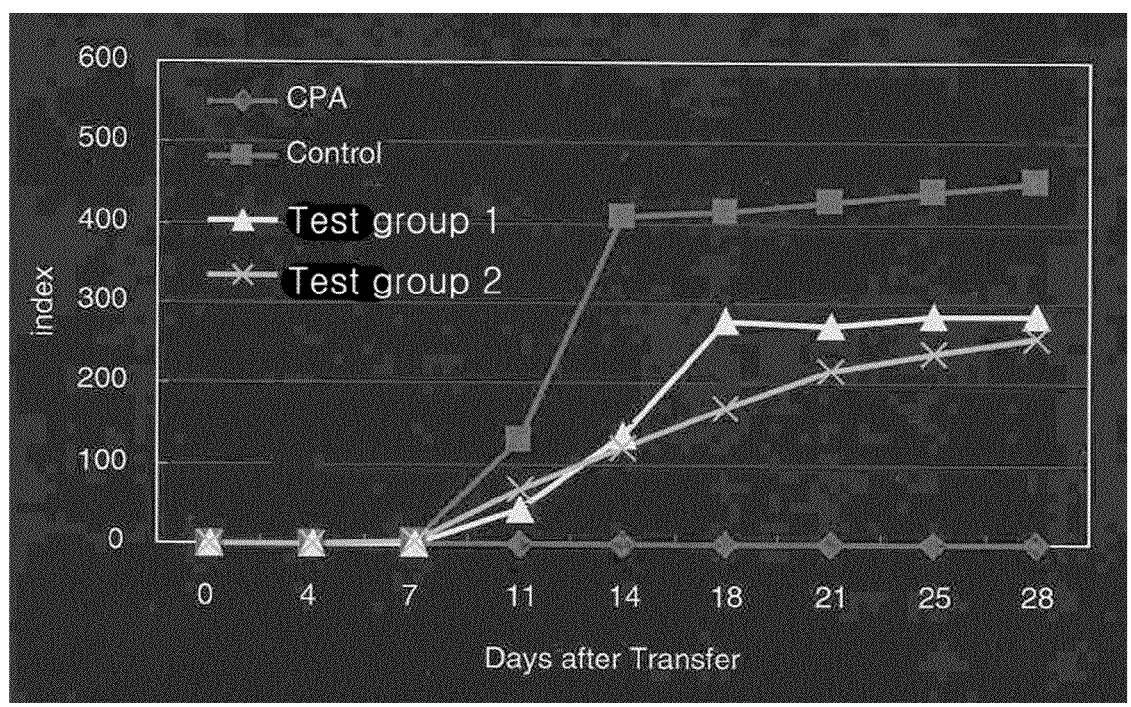
FIG. 5 is a graph showing changes in the weight of the mice administered with the cordyceps mycellia extract of the present invention and with other comparative chemicals in accordance with another embodiment of the present invention.

The results are shown in FIGS. 4 and 5.

In FIG. 4, the levels of the antibodies to the splenocytes were plotted against time for the experimental groups, the control group and the comparative group. FIG. 5 shows changes in weight for the experimental groups, the control group and the comparative group.

As seen in FIG. 4, the production level of antibodies to the transplanted splenocytes was observed to be lower in the mice administered with the cordyceps mycellia extract of the present invention than in the mice administered with CMC only (control). As for ELISA values, a Dunnett's multiple comparison test was performed on the basis of a PBS group.

On Day 11 after the transplantation, there was significance for the experimental group 1 ($p<0.05$), but not significance for the experimental group 2. On Day 14, there was significance for both the experimental group 1 ($p<0.01$) and the experimental group 2 ($p<0.05$). However, no significance was observed for either of them from Day 18. Accordingly, the significant difference on Days 11 and 14 between the experimental group administered with the cordyceps mycellia extract at a dose of 2000 mg/kg and the control group indicates that the cordyceps mycellia extract of the present invention significantly inhibits the production of antibodies responsible for transplant rejection.

For weight change, a Dunnett's multiple comparison test was performed on the basis of the control group. On Day 11 after the transplantation, as shown in FIG. 5, there was significance for the experimental group 1 ($p<0.05$), but not significance for the experimental group 2. On Day 14, there was significance for both the experimental group 1 ($p<0.05$) and the experimental group 2 ($p<0.05$). However, no significance was observed for either of them from Day 18. Accordingly, these results indicate that the cordyceps mycellia extract of the present invention was found to effectively suppress transplant rejection, as demonstrated by the significant difference on Days 11 and 14 between the experimental group administered with the cordyceps mycellia extract at a dose of 2000 mg/kg and the control group.

Furthermore, while the control suffered from skin diseases, such as sores and depilation due to pemphigus, the skin diseases were suppressed in the mice administered with the cordyceps mycellia extract of the present invention. Hence, the cordyceps mycellia extract according to the present invention can be applied to the treatment of skin diseases including atopy, allergic reactions, decubitus ulcers, pemphigus, smallpox, etc.

The composition of the present invention can be prepared as described below.

PREPARATION EXAMPLE 1

Preparation of Pharmaceutical Formulations 1-1. Preparation of Powder

| | |
|---|---|
| *Cordyceps mycellia* extract | 1 g |
| Dextrin | 0.1 g |

The above ingredients were mixed and loaded into an airtight sac to produce powder.

1-2. Preparation of Tablet

| | |
|---|---|
| *Cordyceps mycellia* extract | 500 mg |
| Dextrin | 45 mg |
| Mg Stearate | 5 mg |

These ingredients were mixed and prepared into tablets using a typical tabletting method.

1-3. Preparation of Capsule

| | |
|---|---|
| *Cordyceps mycellia* extract | 500 mg |
| Dextrin | 50 mg |

These ingredients were mixed and loaded into gelatin capsules according to a typical method to produce capsules.

1-4. Preparation of Injection

| | |
|---|---|
| *Cordyceps mycellia* extract | 50 mg/ml |
| Diluted HCl BP | added to form pH 3.5 |
| NaCl BP injection | up to 1 ml |

The cordyceps mycellia extract was dissolved in a suitable volume of an NaCl BP injection, and the solution was adjusted to a pH of 3.5 with diluted HCl BP and to a desired volume with NaCl BP injection, followed by sufficient mixing. The solution was loaded into transparent 5 ml type I ampules, which were hermetically sealed by melting, followed by autoclaving at 120° C. for 15 min to prepare injections.

We claim:

1. A method for inhibiting a transplant organ or tissue rejection in a patient who had the organ or tissue transplanted consisting essentially of administrating a therapeutically effective amount of a mycelia extract from a vegetable worm selected from the group consisting of *Cordyceps militaris, Hymenostilbe odonatae, Cordyceps nutans, Tilachlidiopsis nigra, Paecilomyces japonica, Cordyceps tricentri* and *Cordyceps sphecocephala* to said patient.

2. The method of claim 1, wherein the extract is administered in oral or injection form.

3. The method of claim 1, wherein the extract is orally administered at a dose of 550 to 2,200 mg/day.

4. The method of claim 1, wherein the extract suppresses production of antibodies after organ or tissue transplantation, said antibodies causing transplant rejection.

* * * * *